(12) United States Patent
Vicario et al.

(10) Patent No.: US 12,406,354 B2
(45) Date of Patent: Sep. 2, 2025

(54) METHOD FOR IDENTIFYING A LOG OF ORIGIN OF A FIRST BOARD

(71) Applicant: MICROTEC S.R.L., Bressanone (IT)

(72) Inventors: Enrico Vicario, Martellago (IT); Nicola Conforto, Monselice (IT); Enrico Ursella, Mestre (IT)

(73) Assignee: MICROTEC S.R.L., Bressanone (BZ)

( * ) Notice: Subject to any disclaimer, the term of this patent is extended or adjusted under 35 U.S.C. 154(b) by 474 days.

(21) Appl. No.: 17/879,007

(22) Filed: Aug. 2, 2022

(65) Prior Publication Data

US 2023/0061650 A1    Mar. 2, 2023

(30) Foreign Application Priority Data

Aug. 24, 2021    (IT) .................. 102021000022256

(51) Int. Cl.
*G06T 7/00*      (2017.01)
*G06V 10/54*    (2022.01)
(Continued)

(52) U.S. Cl.
CPC .............. *G06T 7/001* (2013.01); *G06V 10/54* (2022.01); *G06V 10/751* (2022.01); *G06V 20/60* (2022.01);
(Continued)

(58) Field of Classification Search
CPC ........... G06T 7/001; G06T 2207/20084; G06T 2207/30161; G06V 10/54; G06V 10/751; G06V 20/60; G06V 10/82; G01N 33/46; G01N 21/8986; G01N 2021/4735; B27B 1/007; B27G 19/00
See application file for complete search history.

(56) References Cited

U.S. PATENT DOCUMENTS 4,926,350 A *   5/1990   Bechtel .................. G01N 33/46
                                                          209/517
10,987,822 B2    4/2021   Ursella et al.
(Continued)

FOREIGN PATENT DOCUMENTS

DE    102004029252 A1    1/2006
EP        2528716 B1    5/2015
EP        3540426 A1    9/2019

OTHER PUBLICATIONS

Flodin, Jens, et al, "Fingerprint traceability of sawn products using industrial measurement systems for x-ray log scanning and sawn timber surface scanning"; Forest Products Journal, vol. 58, No. 11, (Nov. 2008); pp. 100-105.

*Primary Examiner* — Roy M Punnoose
(74) *Attorney, Agent, or Firm* — Chrisman Gallo Tochtrop LLC (57) ABSTRACT

A method for identifying a log of origin of a first board, comprising an identification step, during which a second board (12) is identified which was obtained from the same log (2) as the first board (11) was obtained from, a studying step, during which identifying features of the second board (12) are identified, and a recognition step during which the log (2) of origin of the first board (11) is recognised, among a plurality of known logs (2) about which saved information is available, and this is done by identifying the log of origin of the second board (12), using the identifying features of the second board (12) itself.

23 Claims, 3 Drawing Sheets

(51) Int. Cl.
   *G06V 10/75*   (2022.01)
   *G06V 20/60*   (2022.01)
   *G06V 10/82*   (2022.01)

(52) U.S. Cl.
   CPC .............. *G06T 2207/20084* (2013.01); *G06T 2207/30161* (2013.01); *G06V 10/82* (2022.01)

(56) References Cited

U.S. PATENT DOCUMENTS

2006/0260718 A1   11/2006   Neglay et al.
2018/0313809 A1*  11/2018   Ursella .................. G01N 33/46
2019/0283266 A1    9/2019   Ursella et al.

* cited by examiner

FIG. 5

METHOD FOR IDENTIFYING A LOG OF ORIGIN OF A FIRST BOARD

FIELD OF THE INVENTION

This invention relates to a method for identifying a log of origin of a first board. Indeed this invention was devised in the context of tracing wooden boards in wood processing plants.

Background of the Invention

As is known, at present logs are cut into boards based on cutting patterns determined by apparatuses capable of inspecting many features of the log, and of picking out the cutting pattern which allows optimisation of the economic value of the wood obtainable with the cutting.

Once the boards have been cut, tracing of their movements inside the processing plant is also known. That allows identification of each board in each processing station, as well as retrieval of information previously saved about each board.

In many applications, identification of the boards in the various processing stations is carried out using, as the identifying element, unique biometric features of the boards. In most applications the unique biometric features are picked out either by means of a visual inspection of the surface, or by means of a radiographic inspection of the internal structure, and they may coincide, for example, with the distribution of knots in the board. The set of unique biometric features of each board is generally defined the "fingerprint".

One of the most widely used tracing methods is described for example in Flodin, Jens, Johan Oja, and Anders Grönlund, "Fingerprint traceability of sawn products using industrial measurement systems for x-ray log scanning and sawn timber surface scanning"; Forest products journal 58.11 (2008); 100-105; it involves picking out the zones in which knots are present on the boards (using video cameras) and comparison of their longitudinal distribution with the known longitudinal distributions of the knots of the logs from which the boards may have been obtained. The longitudinal distributions in the logs are picked out in advance with an X-ray inspection of the logs, before cutting them. Another method of identification of the log of origin of boards which in contrast uses radiographic readings is described in EP 3540426.

The biometric recognition of the boards and of the log from which they were obtained works well to the extent that the boards have the unique biometric features which allow them to be correlated with the log of origin.

However, that technique is not without disadvantages.

The main problem is the fact that, often, the more lateral boards of a log do not have knots, especially in the case of a large log cut from the lower part of a tree. This is due to trimming of the branches, which is often carried out in an artificial way, but more often is done by the plant itself since the lower branches no longer receive enough sunlight. On the other hand, the innermost boards even of logs cut from the lower part of a tree generally have some nodosity linked to the branches which the tree had when it was young and which therefore allow their recognition.

Consequently, often it is not possible to establish a match between the nodosity of the log (or rather, of its innermost part) and that (absent) of the outermost boards obtained from it.

SUMMARY OF THE INVENTION

In this context, the technical purpose which forms the basis of this invention is to overcome the above-mentioned disadvantages.

In particular the technical purpose of this invention is to provide a method for identifying the log of origin even for boards which are without nodosity.

DESCRIPTION OF THE DRAWINGS

Further features and the advantages of this invention will be more apparent in the detailed description, with reference to the accompanying drawings which illustrate several preferred, non-limiting embodiments of a method for identifying a log of origin of a first board, in which.

DETAILED DESCRIPTION OF THE INVENTION

The inventive concept at the basis of this invention was that of determining the origin of a first board 11, without its own features which allow a comparison with the logs 2 of origin, in an indirect way, by picking out first at least one second board 12 which comes from the same log 2 as the first board 11, and then using features of the second board 12 to pick out the log 2 of origin of the second board 12, which will coincide with the log 2 of origin of the first board 11. It should be noticed that picking out of the log 2 of origin of the second board 12 may in itself even be carried out before having verified that the first board 11 and the second board 12 come from the same log 2.

One variant also involves picking out a group of boards 1 coming from the same log 2, also determining their relative positions inside the log 2, and considering the object constituted of the set of all of the boards 1 in the relative positions which they had inside the log 2, to carry out the comparison with the logs 2 previously processed and to thereby determine the log 2 of origin of all of the boards 1 of the group.

Some embodiments of this invention involve determining if two boards 1 were obtained from the same log 2, by inspecting their surface appearance. As is known, each board 1 has six faces in opposite pairs: two end faces 3, two main longitudinal faces 4, and two secondary longitudinal faces 5 (with extent less than or equal to that of the main longitudinal faces 4). Before the boards 1 are cut from a log 2, the end faces 3 belong to an end face 3 of the log 2 (that is to say, to the same cross-section). In contrast, the longitudinal faces 4, 5 are obtained by cutting the log 2 longitudinally according to the predetermined cutting pattern.

As already indicated, a further innovative solution according to this invention is that of establishing a match between boards 1 coming from the same log 2 by observing the outer appearance of their faces. Some embodiments involve comparing either two end faces 3 of two different boards 1, to determine if they were part of the same cross-section of the log 2, or two longitudinal faces 4, 5 of two different boards 1, to understand if they are longitudinal faces 4, 5 which in the log 2 of origin faced, on opposite sides, the same cutting plane. In the first case, if two end faces 3 come from the same cross-section of the log 2, it is possible to verify that the growth rings and the knots present on the surface of the end faces 3 are consistent with each other. In the second case, if two longitudinal faces 4, 5 were generated from the same cutting plane, this means that the wood which constitutes them in the log 2 of origin was only separated by a thickness equal to approximately the thickness of the saw; consequently, it is possible to verify that the surface features (grain, colour and knots, in particular) of the two longitudinal faces 4, 5 are consistent with each other. Indeed, each saw cut which separates two adjacent boards 1 generates two faces whose appearance is very similar (but specular); the degree of similarity is clearer at zones of the two faces in which the discontinuities in the wood (such as the growth rings) extend mainly perpendicularly to the surface of the faces.

In contrast, in some embodiments information is determined about the structure of the wood in the starting log 2 of each board 1, and the structures are compared to determine if two boards 1 were obtained from the same log. In its most general embodiment, the method for identifying a log of origin of a first board 11, comprising an identification step, a studying step and a recognition step.

During the identification step a second board 12 is identified which was obtained from the same log 2 as the first board 11 was obtained from. During the studying step identifying features of the second board 12 are identified. Finally, during the recognition step the log of origin 2 of the first board 11 is recognised, among a plurality of known logs 2 about which saved information is available, and this is done using the identifying features of the second board 12.

In some embodiments, the recognition step is carried out using only the identifying features of the second board 12.

In contrast, in some embodiments, the recognition step is carried out using identifying features both of the first board 11 and of the second board 12, where the identifying features of the first board 11 are also identified during the studying step.

In some embodiments, the identification step comprises a first surface analysis step, a second surface analysis step, and an association step.

The first surface analysis step is a step during which one or more faces of the first board 11 are inspected to determine first information about the first board 11.

Similarly, during the second surface analysis step one or more faces of a second board 12 are inspected to determine second information about the second board 12.

Finally, during the association step the second board 12 is identified as obtained from the same log 2 as the first board 11 was obtained from, by means of the first information and the second information.

In some applications, during the first surface analysis step the one or more faces of the first board 11 are inspected to determine first information about a structure of the wood of a first log from which the first board 11 was obtained. Similarly, during the second surface analysis step the one or more faces of a second board 12 are inspected to determine second information about a structure of the wood of a second log from which the second board 12 was obtained. In this case, the association step comprises within itself a comparison step and a determination step. During the comparison step, the first information and the second information are compared with each other to determine if the structure of the wood of the first log corresponds to the structure of the wood of the second log. During the determination step, in contrast it is established that the first board 11 and the second board 12 were obtained from the same log 2 of origin, if during the comparison step it was determined that the structure of the wood of the first log corresponds to the structure of the wood of the second log.

In some embodiments, during the first surface analysis step and/or during the second surface analysis step, respectively, first information and/or second information about the trend of the growth rings, inside, respectively, the first log and/or the second log are determined. As is known, each growth ring of a log has an internal radius and an external radius which are different from all of the others; even the thickness (the difference between the external radius and the internal radius) of growth rings relative to different years may be different. Consequently, the sequence of the various rings constitutes a sort of unique bar code for each log. In the context of this invention, in terms of structure of the wood, the sequence of growth rings is therefore used. As described in more detail below, it may be determined either by observing the longitudinal faces 4, 5, or the end faces 3.

In some applications, both during the first surface analysis step and during the second surface analysis step, respectively, first information and second information about a trend of the growth rings and/or of the pith inside respectively the first log and the second log are determined. Then, the first information and the second information are used to create a first model and a second model, respectively, of the trend of the growth rings and/or of the pith inside, respectively, the first log and the second log. Finally, during the comparison step the first model and the second model are compared with each other.

In some embodiments, during the first surface analysis step and the second surface analysis step, respectively, first information and second information constituted of images of the texture of the one or more faces of the first board 11 and of the second board 12 are determined. Then, during the comparison step the images of the textures previously determined are compared. Advantageously, in all of the embodiments in which digital images are acquired of the one or more faces of the various boards 1, the digital images are acquired in a band of predetermined frequencies, preferably in the visible band.

In some applications, during the first surface analysis step and/or during the second surface analysis step, the trend of the fibre of the wood at one or more faces, respectively, of the first board 11 and/or of the second board 12 is analysed. Advantageously, that analysis of the trend of the fibre is carried out by analysing the diffusion of the light in the wood (a phenomenon known in the sector as scatter). For that purpose, in the known way for this type of analysis, the face of the board may be illuminated with structured light (fixed or movable) and images of the face illuminated in that way may be acquired to detect the light reflected directly by the surface of the wood, and that emitted after a phenomenon of diffusion along the fibre.

Knowing the trend of the fibre may be useful both to establish a match between faces of different boards 1 (as described in more detail below), and to generate models of the structure of the log 2 from which each board 1, was obtained.

According to one particularly preferred embodiment of this invention, the method also comprises a picking out step carried out before the surface analysis steps.

During the picking out step, in each of the two boards 1 being inspected, one or more reference faces 6 are picked out. The reference faces 6 of both boards 1 are selected, alternatively, either parallel to a main line of extension of the boards 1 (that is to say, in such a way that they are longitudinal faces 4, 5), or perpendicular to that main line of extension (that is to say, in such a way that they are end faces 3).

Figure 4:
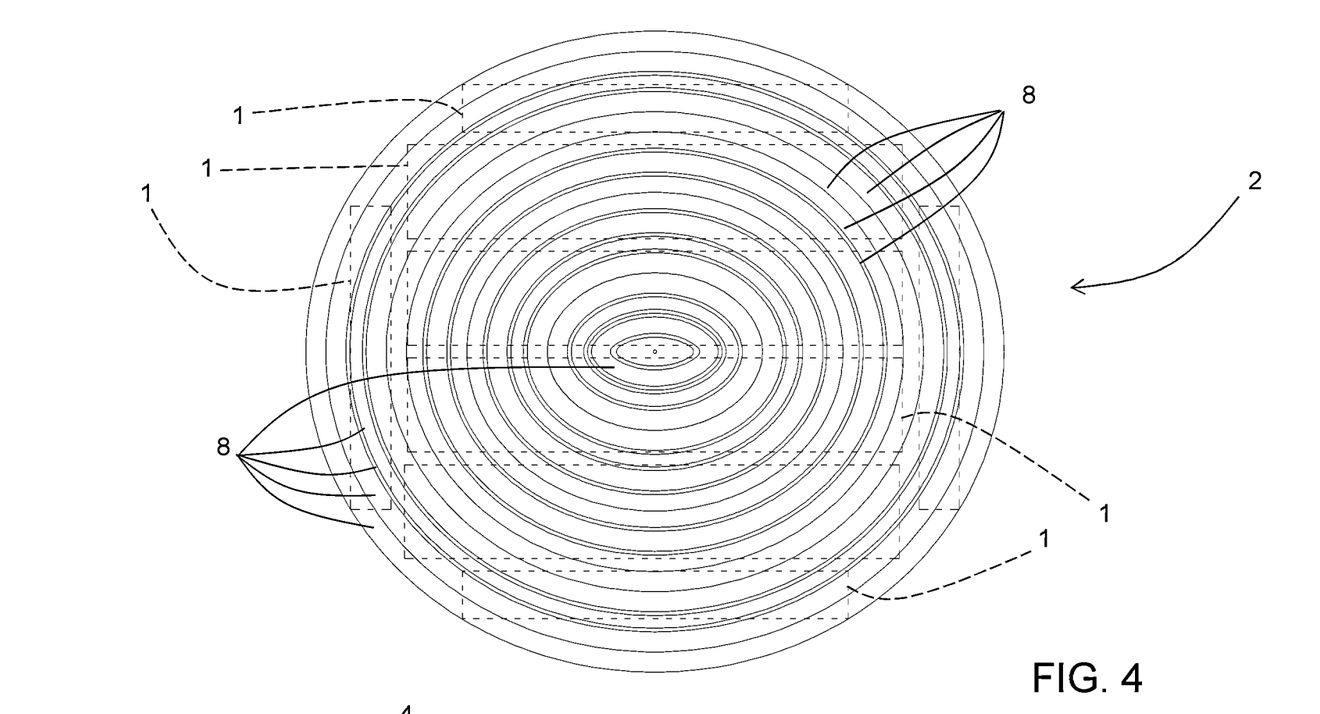
FIG. 4 is a schematic front view of a front face of a log highlighting the growth rings (unbroken lines) and boards obtainable from the log with a predetermined cutting pattern (broken lines)

Given that in most cases the orientation of the boards 1 is unknown, advantageously one or more reference faces 6 may be identified in one board 1 (first board 11) and two or more reference faces 6 in the other board 1 (second board 12). As will become more apparent from the description which follows, if the reference faces 6 are end faces 3, it may be sufficient to identify one reference face 6 in the first board 11 and two reference faces 6 in the second board 12; indeed, in the case of two boards 1 obtained from the same log 2, at least one of the end faces 3 of the second board 12 was part of the same end face 3 of the log 2 to which the end face 3 selected for the first board 11 belonged. Otherwise, since, as illustrated for example in FIGS. 1 and 4, the cutting patterns of the logs 2 may be such as to make from a log 2 both boards 1 with the main longitudinal faces 4 parallel to each other, and boards 1 with the main longitudinal faces 4 perpendicular to each other, it is possible that a main longitudinal face 4 of one board 1 and a secondary longitudinal face 5 of the other board 1 face one cutting plane. In the absence of other information, two boards 1 obtained from the same log 2 of origin may have faced the same cutting plane with any of their longitudinal faces 4, 5. Consequently, it may be necessary to consider all of the longitudinal faces 4, 5 as reference faces 6 of both of the boards 1.

However, in some cases it is possible to carry out a preliminary selection using known information about the cutting patterns used. Indeed, in most wood processing plants the logs 2 are cut with cutting patterns which have a limited number of degrees of freedom. In particular, most plants cut the logs 2 in such a way as to obtain boards 1 with few predetermined sizes. Moreover, often the cutting patterns involve board 1 sizes which are different for the boards 13 obtained from the central cant (such as the four boards 13 at the centre in the case of FIG. 1), the lateral boards 14 parallel to those of the central cant, and the lateral boards 15 perpendicular to those of the central cant. If this information is known, when it is necessary to establish whether or not the first board 11 and the second board 12 were obtained from the same log 2 of origin, by verifying the sizes of the two boards 1 it is often possible to establish if they are boards 1 obtained from a central cant, lateral boards 1 parallel to those of the central cant, or lateral boards 1 perpendicular to those of the central cant. Having established that, it is also possible to know if in the log 2 of origin the two boards 1 to be compared could have faced each other only at the main longitudinal faces 4, at the secondary longitudinal faces 5 or at both. Thanks to that information it is therefore possible to select as reference faces 6 only the longitudinal faces 4, 5 which could have effectively faced each other.

Figure 1:
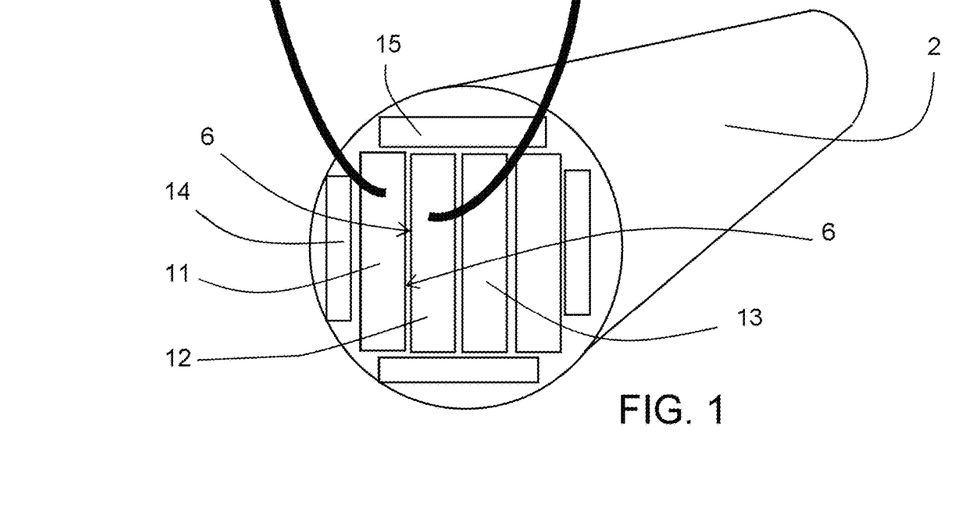
FIG. 1 is a schematic perspective view of a log and the boards obtainable from the log with a predetermined cutting pattern.
Figure 2:
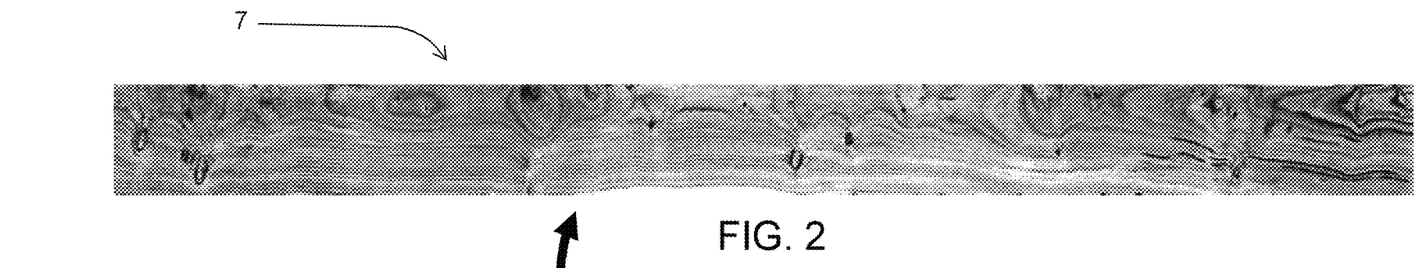
FIGS. 2 and 3 show the photographic images of two faces which face each other, of two adjacent boards of FIG. 1.
Figure 3:
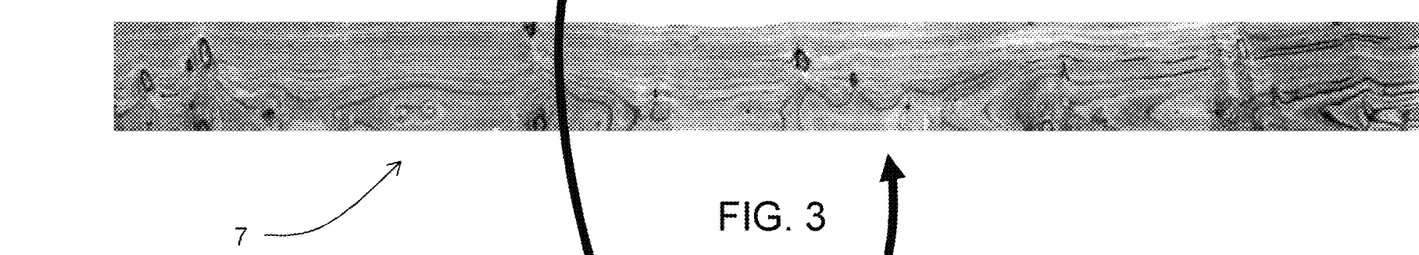

In these embodiments, the first surface analysis step and the second surface analysis step each comprise an acquisition step during which, for each of the one or more reference faces 6 picked out for each board 1, at least one digital image 7 is acquired which shows the entire or part of the outer appearance of the relative reference face 6. Each digital image 7 is part, respectively, of either the first information or of the second information Advantageously, each digital image 7 shows the entire relative reference face 6 and is also corrected to compensate for any distortions due either to the features of the lens, or perspective effects. Preferably the correction is carried out in such a way that the reference face 6 visible in each digital image 7 has proportions substantially identical to the real ones. Moreover, even the dimensions of the images are standardised in such a way that in each digital image 7 each pixel corresponds to the same real dimension (or in such a way that a specific real dimension corresponds to a predetermined number of pixels). Therefore, the digital images appear as illustrated in FIGS. 1 and 2, that is to say, as if they were acquired at each point perpendicularly to the surface of the reference face 6.

If the dimensions of the boards 1 are too big to be able to acquire each digital image 7 with a single snap of a camera, it is also possible that each digital image 7 is obtained by joining together a plurality of secondary images, each of which shows only part of the reference face 6. Moreover, in some applications the digital images may even be acquired using one or more fixed cameras and making the board 1 slide relative to them.

Once all of the digital images 7 necessary have been acquired for the two boards 1 for which a user wants to understand if they were obtained from the same starting log 2, the method comprises carrying out the comparison step. During the comparison step the one or more digital images 7 relative to one board 1, are compared with the one or more digital images 7 relative to the other board 1.

Depending how the reference faces 6 were selected, during the comparison step a different type of comparison is carried out.

If the reference faces 6 of both of the boards 1 are perpendicular to the main line of extension, during the comparison step the digital images 7 of the two boards 1 are compared to assess if the corresponding reference faces 6 were part of the same cross-section of the log 2.

Otherwise, if the reference faces 6 of both of the boards 1 are parallel to the main line of extension, during the comparison step the digital images 7 of the two boards 1 are compared to assess if the corresponding reference faces 6 faced on opposite sides the same cutting plane, that is to say, if they were part of the same piece of log 2 and were separated from each other by a slice of wood with thickness equal to that of a cut made by a saw.

The result of the comparison step may be positive (a match is found—the reference faces 6 of both of the boards 1 were part of the same cross-section of the log 2 or faced on opposite sides the same cutting plane) or negative (no match is found—the reference faces 6 of both of the boards 1 were not part of the same cross-section of the log 2 nor did they face on opposite sides the same cutting plane), and is used in the subsequent determination step. Indeed during the determination step it is established whether or not the two boards 1 were obtained from the same log 2 of origin, and this is done, as already indicated, based on the result of the comparison step. In particular, during the determination step it is established that the two boards 1 were obtained from the same log 2 of origin when the result of the comparison step was positive.

In contrast, if the result of the comparison step was negative, the method comprises repeating the comparison step and the subsequent determination step for a different pair of reference faces 6 of the two boards 1 (using the relative digital images 7). If the result of this second comparison is positive the second time the determination step is carried out it is established that the two boards 1 were obtained from the same log 2 of origin. Otherwise, in the case of a negative result, if there are still pairs of reference faces 6 which can be compared for those two boards 1, the comparison and determination steps are repeated. Preferably, only when there are no more pairs which can be compared, the conclusion is reached that it is impossible to say that the two boards 1 were obtained from the same log 2 of origin. Obviously, that does not mean that the two boards 1 were not obtained from the same log 2 of origin; to verify this it could be necessary to pick out a third board which was obtained either from the same log from which the first board 11 was obtained, or from the same log from which the second board 12 was obtained.

In some embodiments of the method, during the comparison step an inspection is carried out to check for consistency between the surface appearance of the reference face 6 which are compared. The consistency inspection aims to verify if the surface appearance of the reference face 6 of one board 1 is consistent with the surface appearance of the reference face 6 of the other board 1; the consistency is assessed assuming that the two reference faces 6 were, as the case may be, part of the same cross-section of the log 2, or faced on opposite sides the same cutting plane.

If the reference faces 6 of both of the boards 1 are perpendicular to the main line of extension (are end faces 3), in some embodiments, during the consistency inspection there is a comparison of the shape, the thickness, the sequence and/or other features of growth rings 8 of the log 2 which are visible in the digital images 7 relative to a reference face 6 of one board 1 and to a reference face 6 of the other board 1.

Figure 5:
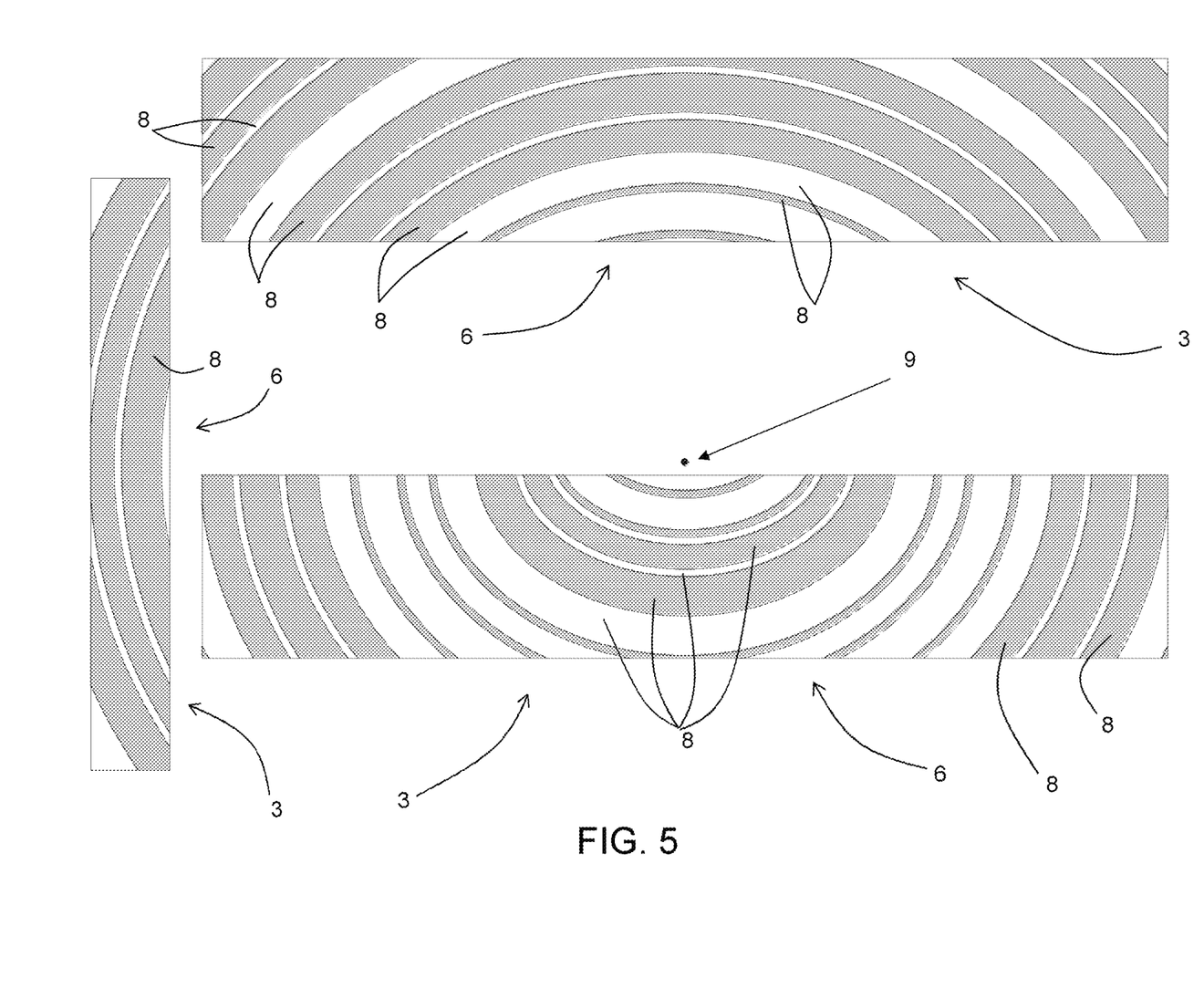
FIG. 5 shows three boards obtained from the log of FIG. 4 highlighting the sequence of growth rings in each of them and the position of the pith of the log.
Figure 6:
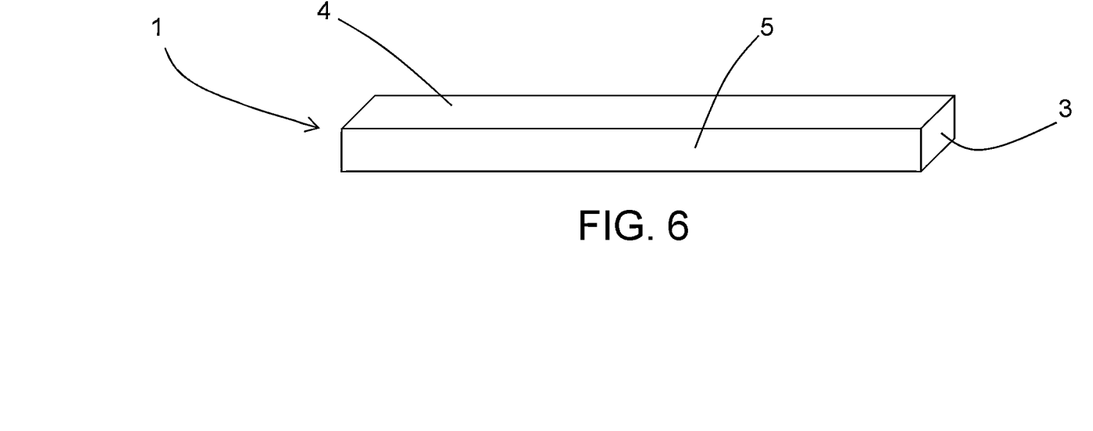
FIG. 6 schematically shows the structure of a board.

In some embodiments, in addition or alternatively to the above, during the consistency inspection, for both of the reference faces 6 there is an estimate of a position of the pith 9 of the log 2 from which the boards 1 were obtained relative to the references faces 6 themselves, and the positions of the pith 9 estimated in this way are compared with each other. The pith 9 may be internal or external relative to the board 1 (FIG. 5).

In some embodiments, in addition or alternatively to the above, during the consistency inspection, for both of the reference faces 6 the shape, the position and the orientation of any knots visible on the reference faces 6 are also considered.

Moreover, in some embodiments, during the comparison step known information about the possible cutting patterns with which the boards 1 were cut is also taken into account. One significant piece of information, for example, is that in the cutting pattern all of the longitudinal faces 4, 5 of the boards 1 are parallel or perpendicular to each other. Consequently, the consistency inspection may be limited to orientations of the reference faces 6 relative to each other, in accordance with which the longitudinal faces 4, 5 are parallel or perpendicular to each other.

In contrast, when the reference faces 6 of both of the boards 1 are parallel to the main line of extension (are therefore longitudinal faces 4, 5), in some embodiments, during the consistency inspection the shape, the position and/or the features of grain and/or knots and/or areas with particular colours visible in the digital image 7 relative to the reference face 6 of one board 1 are compared with those visible in the digital image 7 relative to the reference face 6 of the other board 1, to determine if what is visible in one board 1 may constitute the continuation of what is visible in the other board 1.

In some embodiments, the comparison step is carried out by processing the digital images 7 with a neural network or a deep neural network.

In some embodiments, the consistency inspection is carried out by assigning a consistency score to the pair of digital images 7 compared. The consistency score is advantageously determined in a range of values included between a maximum consistency value and a minimum consistency value. In this case, during the determination step it is determined that the two boards 1 were obtained from the same log 2 when the consistency score is separated from the maximum consistency score by less than a predetermined tolerance.

In general a match score may be used for all of the times the comparison steps are carried out and a match is said to exist when the match score is separated from the maximum match score by less than a further predetermined tolerance.

Once during the determination step it has been determined that two boards 1 were obtained from the same log 2 of origin on the basis of a comparison of the digital images 7 relative to two reference faces 6, there is also an immediate determination of the position that the two reference faces 6, and therefore the two boards 1, occupied relative to each other (the distance is known because it is equal to the width of the cut).

The method described up to now may be implemented either only for two boards 1 for which it is to be verified whether or not they were obtained from the same log 2 of origin, or, advantageously, for a plurality of different boards 1, for example for the purpose of determining which of those boards 1 were obtained from the same log 2 of origin and the relative position of those boards 1 in the log 2 of origin, and relative to each other. Indeed, once the adjacent reference faces 6 of several boards 1 have been virtually coupled, it is possible to transitively group all of the boards 1 which among them have reference faces 6 for which the comparison step gave a positive result, which were therefore generated from the same log 2. In this way it is also possible to understand the position relative to each other from which the boards 1 were extracted. In the case of boards 1 cut with the main longitudinal face 4 orthogonal relative to that of the other boards 1, the digital images 7 of the secondary longitudinal faces 5 of multiple boards 1, may be coupled to a single main longitudinal face 4 of a different board 1.

As can be easily inferred, the method described above may be repeated a plurality of times, for a plurality of different second boards 12, until for at least one of them it is established that it was obtained from the same log 2 from which the first board 11 was obtained.

Another use for the method according to this invention is to identify a log 2 of origin common to a group of boards 1, which can advantageously be applied if each of the boards 1 of the group is without its own fingerprint which allows reliable enough identification of its log 2 of origin.

In this case, the method is carried out a plurality of times, each time with reference to at least one different pair of boards 1 of the group of boards 1, in any case ensuring that the method is carried out at least once for each board 1 of the group. Since it is not generally possible to known a priori which boards 1 are part of the group of boards 1 obtained from the same log 2 of origin, in this case too it is preferably the case that the method is carried out with reference to a plurality of boards 1 which comprises, amongst others, also the boards 1 of the group. Only for the latter, in pairs, the method will give the indication that the log 2 of origin is the same.

Once all of the boards 1 of the group which come from the same log 2 of origin have been identified, the method comprises using the results to create a model of a complex object constituted of the boards 1 of the group for which it was established that the log 2 of origin is the same. In that complex object, the boards 1 of the group will be positioned with an arrangement relative to each other which corresponds to the arrangement relative to each other that the boards 1 had in the log 2 of origin, that arrangement also determined based on the results of the method and on the known information about the thicknesses of the cuts.

At this point, the method comprises, for identifying the log 2 of origin of the group of boards 1, combined used of data relative to the model of the complex object. In other words, the log 2 or origin is not identified by comparing the fingerprint of a single board 1 with that of the log 2, but by calculating a fingerprint of the complex object and using the latter for the comparison with the log 2.

In a further variant, devised to manage cases in which a main longitudinal face 4 of a board 1, in the starting log faced a plurality of secondary longitudinal faces 5, the method comprises using the results of carrying out the various steps for each board 1 to create a partial model of a complex object constituted of a plurality of boards 1 (for example boards 1 which in the cutting pattern were positioned side by side with the main longitudinal faces 4 parallel) with an arrangement relative to each other which corresponds to the arrangement relative to each other of the boards 1 in the log 2 of origin. The partial model generated in this way is then used in place of a first board 11 for further executions of the identification, studying and recognition steps with reference to further second boards 12 of the group (for example for picking out those with perpendicular orientation).

Finally it should be noticed that all of the steps described above are carried out by electronic devices, in particular computers (one or more) for all of the steps which require processing, and image acquisition devices for all of the steps which require them.

This invention brings important advantages.

First of all, thanks to this invention it was possible to provide a method for picking out the log 2 of origin even of boards 1 without their own fingerprint which allows direct identification of the starting log 2.

That method is a useful tool for many applications.

Finally, it should be noticed that this invention is relatively easy to produce and that even the cost linked to implementing the invention is not very high.

The invention described above may be modified and adapted in several ways without thereby departing from the scope of the inventive concept.

All details may be substituted with other technically equivalent elements and the materials used, as well as the shapes and dimensions of the various components, may vary according to requirements.

The invention claimed is:

1. A method for identifying a log of origin of a first board, the method comprising a verification step, carried out by one or more computers, during which the log of origin of the first board is, verified from among a plurality of known logs about which saved information is available;

an identification step, carried out by said one or more computers, during which a second board is identified which was obtained from the same log as the first board was obtained from; and a studying step, carried out by said one or more computers, during which identifying features of the second board are identified;

and wherein the verification step is carried out by said one or more computers, using the identifying features of the second board.

2. The method according to claim 1 wherein the verification step is carried out using only the identifying features of the second board.

3. The method according to claim 1 wherein during the studying step, identifying features of the first board are also identified, and wherein the verification step is carried out using the identifying features both of the first board and of the second board.

4. The method according to claim 1, wherein the identification step comprises the following steps:

a first surface analysis step, carried out by said one or more computers, wherein one or more faces of the first board are inspected to determine first information about the first board;

a second surface analysis step, carried out by said one or more computers, wherein one or more faces of a second board are inspected to determine second information about the second board;

an association step, carried out by said one or more computers, wherein the second board is identified as obtained from the same log as the first board was obtained from by means of the first information and the second information.

5. The method according to claim 4, wherein:

during the first surface analysis step the one or more faces of a first board are inspected to determine first information about a structure of the wood of a first log from which the first board was obtained;

during the second surface analysis step the one or more faces of a second board are inspected to determine second information about a structure of the wood of a second log from which the second board was obtained;

the association step comprises a comparison step, carried out by said one or more computers, during which the first information and the second information are compared with each other to determine if the structure of the wood of the first log corresponds to the structure of the wood of the second log, and a determination step, carried out by said one or more computers, during which it is established that the first board and the second board were obtained from the same log of origin if during the comparison step it was determined that the structure of the wood of the first log corresponds to the structure of the wood of the second log.

6. The method according to claim 5, wherein during the first surface analysis step and/or the second surface analysis step respectively first information and/or second information about a trend of growth rings inside respectively the first log and/or the second log are determined.

7. The method according to claim 6, wherein during the first surface analysis step and the second surface analysis step respectively first information and second information about a trend of growth rings and/or of a pith inside respectively the first log and the second are determined, and wherein the first information and the second information are used to create a first model and a second model, respectively, of the trend of the growth rings and/or of the pith inside, respectively, the first log and the second log, and wherein during the comparison step the first model and the second model are compared.

8. The method according to claim 5 wherein during the first surface analysis step and the second surface analysis step respectively first information and second information constituted of images of the texture of the one or more faces of the first board and of the second board are determined, and wherein during the comparison step the images of the textures are compared.

9. The method according to claim 4, wherein during the first surface analysis step and/or the second surface analysis step digital images acquired in a band of predetermined frequencies of the one or more faces, respectively, of the first board and/or of the second board are analysed.

10. The method according to claim 4, wherein during the first surface analysis step and/or the second surface analysis step the trend of the fibre of the wood at the one or more faces, respectively, of the first board and/or of the second board is analysed by said one or more computers, by means of an analysis of diffusion of light in the wood.

11. The method according to claim 4, also comprising a picking out step, carried out by said one or more computers, during which there is picking out, in each of the two boards, of one or more reference faces, wherein the reference faces of both of the boards are, alternatively, either parallel to a main line of extension of the boards, or perpendicular to that main line of extension, wherein moreover:
the first surface analysis step and the second surface analysis step each comprise an acquisition step, carried out by an image acquisition device, during which, for each of the one or more reference faces of the respective board, digital images are acquired which show the entire or part of the outer appearance of the reference faces and which are part respectively of the first information and of the second information; and
during the comparison step, a digital image of the one or more reference faces of one board, is compared by said one or more computers with a digital image of the one or more reference faces of the other board;
and wherein during the comparison step:
if the reference faces of both of the boards are perpendicular to the main line of extension, the digital images of the two boards are compared by said one or more computers to assess if the corresponding reference faces were part of the same cross-section of the log; or
if the reference faces of both of the boards are parallel to the main line of extension, the digital images of the two boards are compared by said one or more computers to assess if the corresponding reference faces faced on opposite sides the same cutting plane, and wherein, during the determination step, it is established by said one or more computers that the two boards were obtained from the same log of origin when during the comparison step it was determined, alternatively and respectively, either that the reference faces of both of the boards were part of the same cross-section of the log, or that the reference faces of both of the boards faced on opposite sides the same cutting plane.

12. The method according to claim 11 wherein during the comparison step a consistency inspection of the surface appearance of the reference faces is carried out by said one or more computers.

13. The method according to claim 12, wherein, if the reference faces of both of the boards are perpendicular to the main line of extension, during the consistency inspection there is a comparison of the shape, the thickness, the sequence and/or other features of growth rings of the log which are visible in the digital images relative to a reference face of one board and to a reference face of the other board.

14. The method according to claim 12, wherein, if the reference faces of both of the boards are perpendicular to the main line of extension, during the consistency inspection for both of the boards there is an estimate of a position of the pith of the log from which the boards were obtained, relative to the boards themselves, and the positions of the pith estimated in this way are compared with each other.

15. The method according to claim 12, wherein, if the reference faces of both of the boards are parallel to the main line of extension, during the consistency inspection the shape, the position and/or other features of grain and/or knots visible in the digital images relative to a reference face of one board are compared with those visible in the digital images relative to a reference face of the other board, to determine if they are faces which in the log faced on opposite sides the same cutting plane.

16. The method according to claim 12, wherein, if the reference faces of both of the boards are parallel to the main line of extension, during the consistency inspection the shape, the position, the colour of areas visible in the digital images relative to a reference face of one board are compared with those of areas visible in the digital images relative to a reference face of the other board, to determine if they are faces which in the log faced on opposite sides the same cutting plane.

17. The method according to claim 11, wherein the comparison step is carried out by processing the digital images with a neural network or a deep neural network.

18. The method according to claim 12, wherein the consistency inspection is carried out by assigning a consistency score to the pair of digital images compared, the consistency score being determined in a range of values included between a maximum consistency value and a minimum consistency value, and wherein during the determination step it is determined that the two boards were obtained from the same log when the consistency score is separated from the maximum consistency score by less than a predetermined tolerance.

19. The method according to claim 11, wherein, during the picking out step there is picking out, by said one or more computers and in at least one of the two boards, of two or more reference faces, and wherein, when during the comparison step it was determined by said one or more computers that the reference faces compared were not part of the same cross-section of the log nor did they face on opposite sides the same cutting plane, the comparison step and the determination step are repeated by said one or more computers for a different pair of reference faces.

20. The method according to claim 1, wherein a position of the second board inside the log of origin is also picked out by said one or more computers and wherein a relative position of the first board in the log of origin relative to the second board is determined and, based on this, a position of the first board in the log of origin is determined by said one or more computers.

21. The method according to claim 1 wherein the identification step, the studying step, and the verification step are carried out a plurality of times for each second board of a group of second boards, wherein moreover the results of the method are used by said one or more computers to create a model of a complex object constituted of the first board and of the boards of the group for which it was established that the log of origin is the same, with an arrangement relative to each other which corresponds to an arrangement relative to each other of the boards in the log of origin, and wherein data about the model generated in this way are used by said one or more computers as a whole to identify the log of origin.

22. The method according to claim 21, wherein moreover the results of the method are used by said one or more computers to create a partial model of a complex object constituted of the first board and of some of the boards of the group for which it was established that the log of origin is the same, with an arrangement relative to each other which corresponds to an arrangement relative to each other of the boards in the log of origin, and wherein the partial model generated in this way is used by said one or more computers as a first board for further executions of the identification, studying and verification steps with reference to further second boards of the group.

23. A method for identifying a log of origin of a first board, the method comprising a verification step, carried out by one or more computers, during which the log of origin of the first board is verified from a plurality of known logs which saved information is available;

an identification step, carried out by said one or more computers, during which a second board is identified which was obtained from the same log as the first board was obtained from, wherein the identification step comprises a first surface computerized analysis step that inspects a digital image of a face of the first board to generate first data about the first board, a second surface computerized analysis step that inspects a second digital image of a face of the second board to generate second data about the second board; and a studying step, carried out by said one or more computers, during which identifying features of the second board are identified;

an association step, carried out by said one or more computers, wherein the second board is identified as obtained from the same log as the first board was obtained from by means of the first data and the second data;

and wherein the verification step is carried out by said one or more computers, using the identifying features of the second board.

* * * * *